(12) United States Patent
Woodruff et al.

(10) Patent No.: US 8,481,026 B1
(45) Date of Patent: Jul. 9, 2013

(54) BACTERIA WITH INCREASED TREHALOSE PRODUCTION AND METHOD FOR USING THE SAME IN BIOREMEDIATION

(76) Inventors: Peter J. Woodruff, Brunswick, ME (US); Tamlyn M. Frederick, Brunswick, ME (US)

( * ) Notice: Subject to any disclaimer, the term of this patent is extended or adjusted under 35 U.S.C. 154(b) by 419 days.

(21) Appl. No.: 12/762,023

(22) Filed: Apr. 16, 2010

Related U.S. Application Data

(60) Provisional application No. 61/170,411, filed on Apr. 17, 2009.

(51) Int. Cl.
*A01N 63/00* (2006.01)
*A01N 65/00* (2009.01)
*A61K 48/00* (2006.01)

(52) U.S. Cl.
USPC ........... 424/93.4; 424/9.1; 424/9.2; 424/93.1; 424/93.462; 424/241.1; 424/257.1; 435/41; 435/69.1

(58) Field of Classification Search
USPC .................... 424/9.1, 9.2, 93.1, 93.4, 93.462, 424/241.1, 257.1; 435/41, 69.1
See application file for complete search history.

(56) References Cited

U.S. PATENT DOCUMENTS 6,133,034 A * 10/2000 Strom et al. .................. 435/419

OTHER PUBLICATIONS

Pieper, DH and Reineke, W, Engireedng Bacteria for Bioremediation, Current Opinion in Biotechnology, 2000, vol. 11, pp. 262-270.
Deleo, PC and Ehrlich, HL., Reduction of hexavalent chromium by *Pseudomonas fluorescens* LB300 in batch and continuous cultures, Applied Microbiology and Biotechnology, 1994, vol. 40, pp. 756-759.
Benaroudj, N. et al, Trehalose Accumulation During Cellular Stress Protects Cells and Cellular Proteins from Damage by Oxygen Radicals, J. of Biological Chemistry, 2001, vol. 216, No. 26, Issue of Jun. 29, pp. 24261-24261.
Kandror, O et al, Trehalose synthesis is induced upon exposure of *Escherichia coli* to cold and is essential for viability at low temperatures, Proc. Natl. Acad. Sci., 2002, vol. 99, pp, 9727-9732.
Glaever, HM et al, Biochemical and Genetic Characterization of Osmoregulator Trehalose Synthesis in *Escherichia coli*, J. of Bacteriology, 1988, Vol 170, pp. 2841-2849.
Alvarex-Peral, FJ et al, Protective role of trehalose during severe oxidative stress caused by hydrogen peroxide and the adaptive oxidative stress response in *Candida albicans*, Microbiology, 2002, vol. 148, pp. 2599-2606.
Garg, AK et al, Trehalose accumulation in rice plants confers high tolerance levels to different abiotic stresses, Proc. Natl. Acad. Sci., 2002, vol. 99, pp. 15898-15903.
Woodruff, PJ et al., Trehalose is Required for Growth of *Mycobacterium smegmatis*, J. of Biological Chemistry, 2004, vol. 279, No. 28, Issue of Jul. 9, pp. 28835-28843.
Camargo, Fao et al, Chromate Reduction by Chromium-Resistant Bacteria Isolated from Soils Contaminated with Dichromate, J. of Environ. Qual., 2003, vol. 32, pp. 1228-1233.
Lofroth, G and Ames, BN, Mutagenicity of inorganic compounds in *Salmonella typhimurium*: arsenic, chromium and selenium, Mutation Res., 1978, vol. 43, pp. 65-66.
Ackerly, DF et al, Effect of Chronicle Stress on *Escherichia coil* K-12, 2006, J. of Bacteriology vol. 188, pp. 3371-3381.
Venosa, AD et al. Bioremediation of an Experimental Oil Spill on the Shoreline of Delaware Bay, Environ. Sci. Technol., 1996, vol. 30, pp. 1764-1775.
Finneran, KT et al, Potential for Bioremediation of Uranium-Contaminated Acquifers with Microbial U(VI) Reduction, Soil and Sediment Contamination, 2002, vol. 11. pp. 339-357.
Crowe, JH, *Anydrobiosis*, Annu. Rev. Physiol., 1992, vol. 54, pp. 579-599.

* cited by examiner

*Primary Examiner* — Rodney P. Swartz
(74) *Attorney, Agent, or Firm* — Verrill Dana, LLP; Chris A. Caseiro

(57) ABSTRACT

Bacteria with improved survival under toxic and oxidative stress and methods of using the same for bioremediation are described. Many bacteria such as *Escherichia coli* have been found to naturally reduce toxic pollutants into a less toxic form, such as by reducing Chromium (VI) to Chromium (III). Reducing such toxins generates damaging reactive oxygen species, so it is important to find a defense for these bacteria against the associated oxidative stress. Trehalose is a small biomolecule that has been shown to protect bacteria from various types of stress by accumulating within the cells. The present invention is directed to bacteria genetically modified to overexpress trehalose biosynthesis genes. The bacteria demonstrate improved viability when challenged with toxins and oxidative stress. The present invention provides inexpensive and beneficial bacteria and methods for environmental remediation.

25 Claims, 6 Drawing Sheets

BACTERIA WITH INCREASED TREHALOSE PRODUCTION AND METHOD FOR USING THE SAME IN BIOREMEDIATION

CROSS-REFERENCE TO RELATED APPLICATION

The present invention relates to, and claims priority in, U.S. Provisional Patent Application Ser. No. 61/170,411, entitled "SYSTEM AND METHOD FOR INCREASED TREHALOSE PRODUCTION IN BACTERIA TO EXPEDITE BIOREMEDIATION OF HEXAVALENT CHROMIUM" filed Apr. 17, 2009 by the same inventors. The contents of the related application are incorporated herein by reference.

REFERENCE TO SEQUENCE LISTING

The present invention incorporates by reference the information in the "seqlist.txt" file (1.19 kb), which is ASCII compatible and was created on Apr. 16, 2010. This file contains sequence information for SEQ ID NOs: 1-6 referenced in the Detailed Description of the Invention below.

FIELD OF THE INVENTION

The present invention relates to bacteria with improved survival under toxic and oxidative stress. These bacteria and methods of using the bacteria are useful for improved, inexpensive environmental bioremediation. More particularly, the present invention relates to systems and methods for overexpressing trehalose biosynthesis genes in bacteria and using the bacteria in bioremediation.

BACKGROUND OF THE INVENTION

Bioremediation is a process by which living organisms prevent or reduce the negative effects of toxins and pollutants in the environment. It has emerged as an effective yet relatively inexpensive way to clean up toxic waste sites and polluted environments. Bioremediation can be applied to a wide range of toxins in various environments and has consequently become the focus of much attention. Bioremediation is desirable due to its relatively low cost, its effectiveness, and because it utilizes living organisms that are native to the site of remediation. As a non-limiting example of a pollutant suitable for bioremediation, Chromium (VI) is extremely toxic, carcinogenic, and mutagenic, but commonly enters the soil and groundwater as an unwanted byproduct of industrial processes. Therefore, it is important to develop techniques to remediate contaminated areas containing this toxin.

Many naturally occurring bacteria have been found to detoxify the environment by reducing toxins such as Uranium (VI) to Uranium (IV), Arsenic (VI) to Arsenic (III), Lead (II) to Lead (0), and Chromium (VI) to Chromium (III). Reducing these contaminants makes them less soluble and less, likely to contaminate water supplies.

While many bacteria such as *Escherichia coli* (*E. coli*) have a natural ability to detoxify contaminated surroundings and create habitable environments, current research aims to improve the detoxification capabilities of these bacteria by increasing their viability in toxic environments. By increasing viability, their detoxification power becomes more effective, and thus reasonably low quantities of these microorganisms could be successfully applied to large-scale clean ups. Therefore, it is important to explore the roles and applications of various molecules and enzymes that can be manipulated in these bacteria to enhance bioremediation. A particularly interesting molecule that has tremendous potential in this field is trehalose, a sugar that has been found to improve survival of toxin-exposed organisms.

Trehalose, which is found in plants, animals, and some microorganisms, is a compatible solute composed of two $\alpha$, $\alpha$, 1, 1 linked glucose molecules. Compatible solutes are small molecules that can build up in high concentrations without disrupting normal biological processes. This accumulation protects cells against damage from desiccation, high salt concentrations, oxidative stress, or extreme thermal conditions. Trehalose is a unique molecule in that it appears to protect against each of these types of stresses. In bacteria, trehalose accumulates as a biological adaptation to resist stress. Trehalose is therefore particularly attractive for the field of bioremediation because of its potential to facilitate improved bioremediation through protection of bacteria from different types of pollutants and toxins causing stress.

A number of trehalose biosynthesis pathways are naturally found in different microorganisms. Many bacteria such as *E. coli* contain only the OtsA/OtsB pathway which generates trehalose from glucose-6-phosphate and UDP-glucose (FIG. 1). The OtsA enzyme is responsible for production of trehalose-6-phosphate synthase while OtsB encodes trehalose-6-phosphate phosphatase. Other organisms such as *Mycobacterium smegmatis* (*M. smegmatis*) contain multiple trehalose biosynthesis genes such as TreY/TreZ and TreS in addition to the OtsA/OtsB pathway. The TreY/TreZ pathway generates trehalose using maltoheptose, with the TreY gene encoding maltooligosaccharyltrehalose synthase and the TreZ encoding maltooligosaccharyltrehalose trehalohydrolase (FIG. 1). The TreS pathway uses trehalose synthase to generate trehalose from maltose (FIG. 1). The presence of multiple pathways indicates the integral role of trehalose in the survival of these bacteria.

Researchers have devised numerous schemes to enhance bioremediation by increasing the rate at which it occurs. However, the quest remains to achieve more effective bioremediation through development of methods that significantly improve the detoxification capabilities of bacteria.

Previous studies have demonstrated that *E. coli* is capable of reducing the toxin Chromium (VI) to its much less toxic form Chromium (III). Chromium is commonly used in the production of nuclear weapons and for many industrial purposes, and is thus a prevalent environmental contaminant. Chromium (VI) is highly soluble and extremely toxic, carcinogenic, and mutagenic. To minimize the detrimental effects of this contaminant it can be reduced by microorganisms to its trivalent form, which is known to be less soluble and 1000-fold less mutagenic. However, reducing Chromium from its hexavalent to trivalent state generates reactive oxygen species (hydroxyl radicals) that are damaging to bacteria. Therefore, it is important to defend these bacteria from the associated oxidative stress in order to maintain or increase the rate of bioremediation. Given the protective nature of trehalose, increased trehalose production should provide bacteria with an added defense against the oxidative stress generated from Chromium (VI) reduction.

SUMMARY OF THE INVENTION

The overall purpose of this invention is to improve the efficiency of bioremediation by increasing trehalose production in bacteria. This invention increases the resistance of bacteria to oxidative stresses caused by toxins by increasing the amount of trehalose production in the bacteria. Trehalose production may be increased through genetic engineering of the bacteria to include additional copies of endogenous or exogenous trehalose biosynthesis genes, or by directed evolution of endogenous trehalose biosynthesis genes.

Bacteria have much higher levels of resistance to toxins such as Chromium (VI) than humans and other animals. They are able to take up chromate by their sulfate or phosphate transport systems, ultimately reducing this toxin to its less threatening form. Providing bacteria with heightened defenses against various types of stress to promote viability in unfavorable circumstances is a major focus in the field of bioremediation. Genetic engineering has been used recently in the field of bioremediation to generate bacteria that have increased bioremediation capabilities. Trehalose is a small biomolecule that protects bacteria from pH, osmotic, thermal, and oxidative stress by accumulating in the bacteria.

The present invention takes advantage of the protective nature of trehalose accumulation and introduces multiple trehalose biosynthetic pathways into bacteria to bolster their defenses against toxic and oxidative stress in extreme environments. This is a novel approach to improving the rate and effectiveness of bioremediation, as previous studies have used techniques such as providing bacteria with increased nutrients to promote growth, or genetically engineering bacteria with enzymes for increased electron transfer. However, these methods fail to provide microorganisms with improved defense mechanisms against stress associated with the toxins they reduce.

Surprisingly, the present invention discloses that isopropyl-β-D-thio-galactoside (IPTG) is toxic to stressed bacteria. Thus, the benefits of trehalose accumulation are offset by the detrimental effects of adding more IPTG to induce trehalose accumulation. As such, the present invention teaches that trehalose production should be increased either with alternative induction systems (such as arabinose) or alternative methods (such as by carrying out directed evolution) in order to optimize the bioremediation and viability characteristics of the genetically modified bacteria.

The present invention also discloses the surprising discovery that, contrary to what was known in the art, showing that both osmotic and thermal stress activate trehalose biosynthesis, oxidative stress exerted on E. coli does not induce trehalose synthesis. As such, trehalose biosyntheis must be induced artificially in order to have a protective effect when bacteria are challenged with toxins that result in oxidative stress. This discovery allows bacteria such as E. coli to be successfully used for bioremediation.

The present invention may be useful for bioremediation of other types of pollutants or toxins which can be broken down by bacteria. In one embodiment, the present invention is used for bioremediation of Chromium (VI). In another embodiment it is used for bioremediation of Uranium (VI).

Any suitable bacteria useful for bioremediation may be used in the present invention. The bacteria may or may not have endogenous trehalose biosynthetic pathways. In one embodiment the bacteria is E. coli. In another embodiment the bacteria is a soil bacteria such as Bactillus subtilis (B. subtilis). In another embodiment the bacteria are found at field sites which may be contaminated, such as Shewanella onesidensis (S. onesidensis) or Geobacter metallireducens (G. metallireducens).

Any suitable trehalose biosynthesis genes may be cloned into the bacteria to increase production and accumulation of trehalose. In one embodiment, the genes encode the enzymes of the OtsA/OtsB pathway. In another embodiment, the genes encode the enzymes of the TreY/TreZ pathway. In another embodiment, the genes encode the enzymes of the TreS pathway. In another embodiment, the genes encode the enzymes from more than one trehalose biosynthesic pathway. The sequences of the genes and operons encoding the enzymes of the trehalose biosynthetic pathways are known in the art.

In the present invention, the viability of bacteria is increased by cloning extra trehalose biosynthesis genes into the bacteria. In one embodiment, trehalose biosynthesis genes from an exogenous source are cloned into a target bacteria. For example, in a preferred embodiment, trehalose synthesis genes from M. smegmatis are cloned into E. coli. In another embodiment, the bacteria overexpresses its endogenous trehalose biosynthesis genes. For example, in a preferred embodiment, E. coli may be overexpressing the OtsA/OtsB trehalose biosynthesis genes. In another embodiment, genes from more than one source may be combined into a target bacteria. For example, in a preferred embodiment OtsA/OtsB trehalose biosynthesis genes from E. coli and the TreS and TreY/TreZ genes from M. smegmatis may be cloned into B. subtilis.

The genes encoding the enzymes from a desired trehalose biosynthesic pathway are cloned into suitable bacteria using standard methods known in the art. All reagents, cell lines, and plasmids used in the process are commercially available and known in the art. For example, genes from a trehalose biosynthetic pathway can be amplified using a polymerase chain reaction (PCR) with the appropriate primers from the genomic deoxyribonucleic acid (DNA) of a wild type bacteria endogenously containing the genes or from plasmids containing the genes by cloning. The products from the PCR amplification are purified and inserted into a suitable plasmid using restriction enzymes. The plasmids are then used to transform suitable bacteria, and the bacteria are cultured and tested for production of trehalose. The transformed bacteria can be challenged with toxins to determine their viability and bioremediation capabilities.

Bacteria that produce higher levels of trehalose are more useful than wild type bacteria for bioremediation. For example, increased trehalose production improves E. coli viability and increases the rate of Chromium (VI) reduction. This is presumably because the trehalose protects these bacteria from hydroxyl radicals produced during Chromium (VI) reduction. Genetically modified bacteria may be used for bioremediation in an environment in situ. In this embodiment the genetically modified bacteria and appropriate inducer would be introduced directly to the environment. Alternatively, bioremediation may be carried out by adding genetically engineered bacteria and an appropriate inducer to a bioreactor with contaminated soil, waiting for the bacteria to detoxify the soil, sterilizing the soil to kill the genetically engineered bacteria, and then returning the soil to the ground.

These and other advantages and aspects of the bacteria and methods of the present invention will become apparent upon review of the following detailed description, the accompanying drawings, and the appended claims.

DETAILED DESCRIPTION OF THE INVENTION

The invention will be described in detail by means of the following examples. It is to be understood that the underlying ideas and techniques could be used with other trehalose biosynthetic pathways, bacteria, and pollutants for bioremediation without departing from the scope of the invention. All reagents were obtained from Sigma Chemicals (St. Louis, Mo.) unless otherwise stated.

Figure 1:
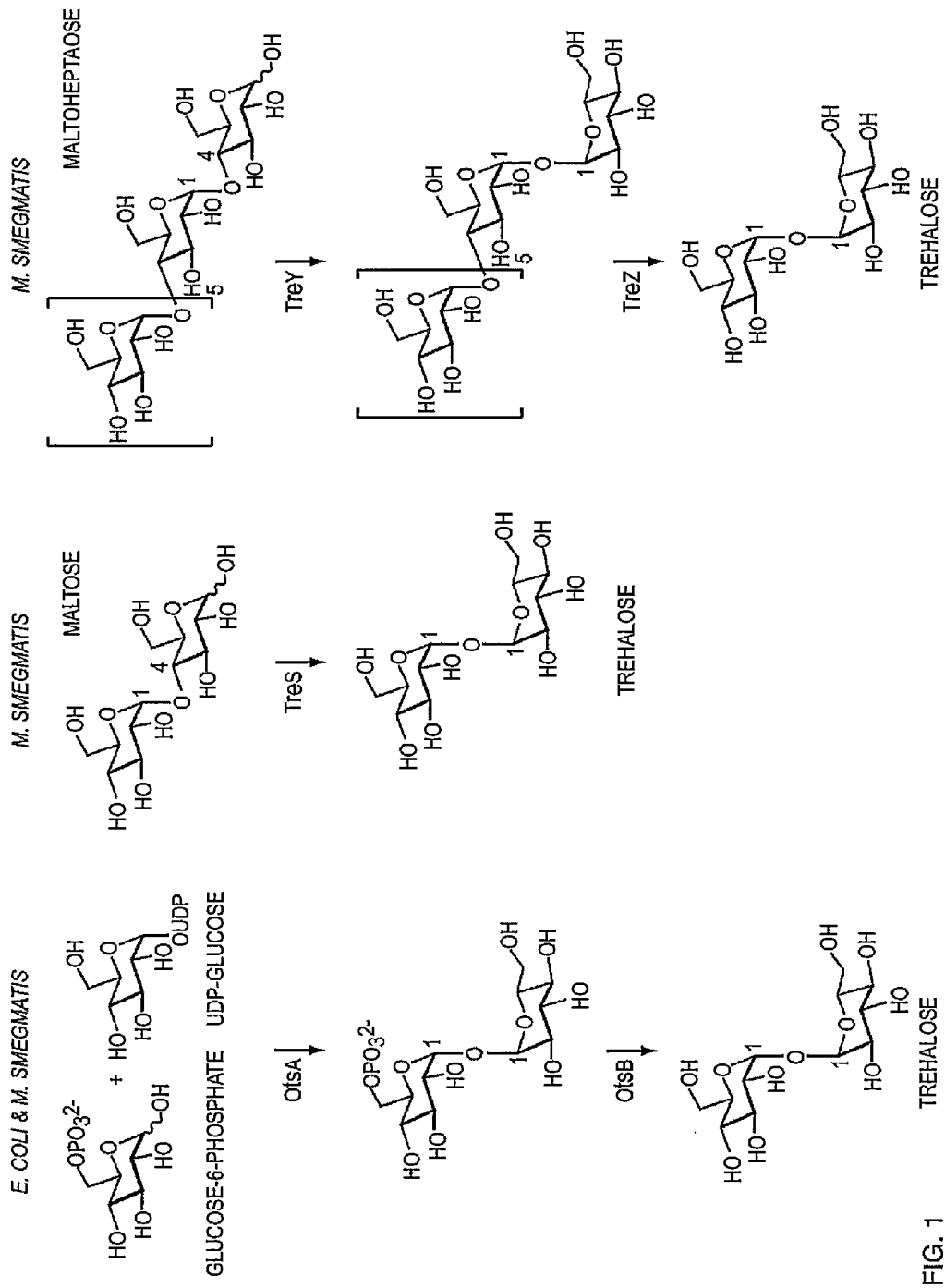
FIG. 1 illustrates the three major pathways for trehalose biosynthesis. E. coli has only the OtsA/OtsB genes while M. smegmatis has the TreS and TreY/TreZ genes in addition to the OtsA/OtsB genes.
Figure 2:
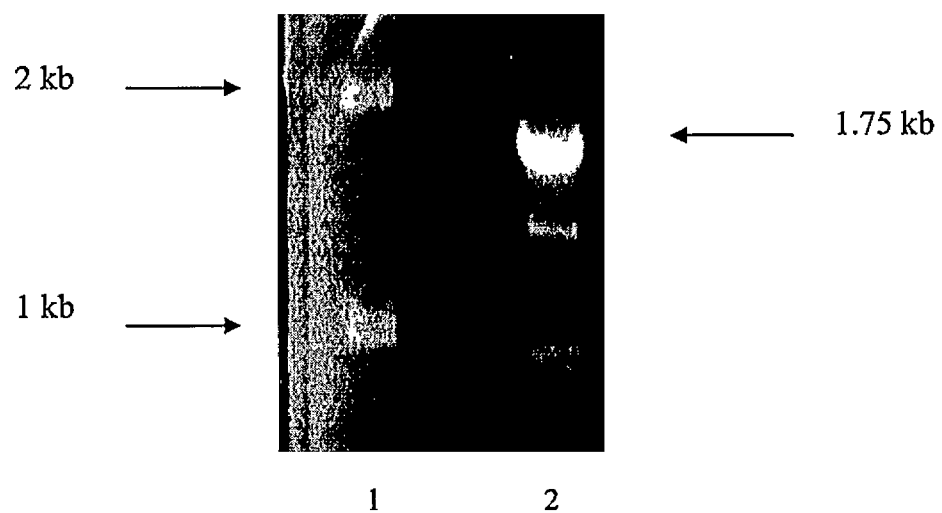
FIG. 2 illustrates the TreS trehalose biosynthesis gene amplified from M. smegmatis. The TreS gene (lane 2) appears at approximately 1.75 kb as indicated by the DNA ladder (lane 1).

The TreS trehalose biosynthesis pathway from *M. smegmatis* was selected for cloning. Purified *M. smegmatis* genomic DNA was used as a template, and PCR amplification of the TreS gene was conducted using Pfu AD DNA Polymerase (New England Biolabs; Ipswitch, Mass.), 10% dimethyl sulfoxide (DMSO), and the 3' TreS and 5' TreS primers. The 3' TreS and 5' TreS primer (New England Biolabs; Ipswitch, Mass.) sequences were 5'ATTAGGTACCTCATTGCTGCGCTCC 3' (SEQ ID NO: 1) and 5'ATTAGCTAGCATGGAGGAGCACACG 3' (SEQ ID NO: 2) respectively. The PTC-100 Thermocycler (MJ Research; Waltham, Mass.) performed a segment at 95° C. for 5 minutes followed by 25 cycles at 95° C. for 1 minute, 55° C. for 45 seconds, and 72° C. for 2 minutes with a final extension at 72° C. for 10 minutes. The product was characterized using agarose gel electrophoresis. FIG. 2 shows the PCR product of the TreS gene at approximately 1.75 kb, as expected.

Similar protocols were followed for PCR amplification of the TreY/TreZ trehalose biosynthetic genes from *M. smegmatis*. Using purified *M. smegmatis* genomic DNA as a template, PCR amplification of the TreY/TreZ genes was conducted using Pfu AD DNA Polymerase (New England Biolabs; Ipswitch, Mass.), 10% DMSO, and the 3' TreZ and 5' TreY primers. The 3' TreZ and 5' TreY primer (New England Biolabs; Ipswitch, Mass.) sequences used were 5'ATTACCTGCAGGCCCGGCTGCGGAT 3' (SEQ ID NO: 3) and 5'ATTAGCTAGCATGACGCGCCCGGTG 3' (SEQ ID NO: 4) respectively. The PTC-100 Thermocycler (MJ Research; Waltham, Mass.) performed a segment at 95° C. for 5 minutes followed by 25 cycles at 95° C. for 1 minute, 55° C. for 45 seconds, and 72° C. for 4 minutes with a final extension at 72° C. for 10 minutes. The product was characterized using agarose gel electrophoresis.

Similar protocols would be followed to clone any trehalose biosynthetic pathway, such as the OtsA/OtsB pathway. For example, the OtsA/OtsB pathway can be cloned from a plasmid containing the pathway by using purified pET-OtsA/OtsB plasmid as a template. The OtsA/OtsB genes could also be cloned from genomic DNA of bacteria which contain this endogenous pathway, such as *E. coli*.

Figure 3:
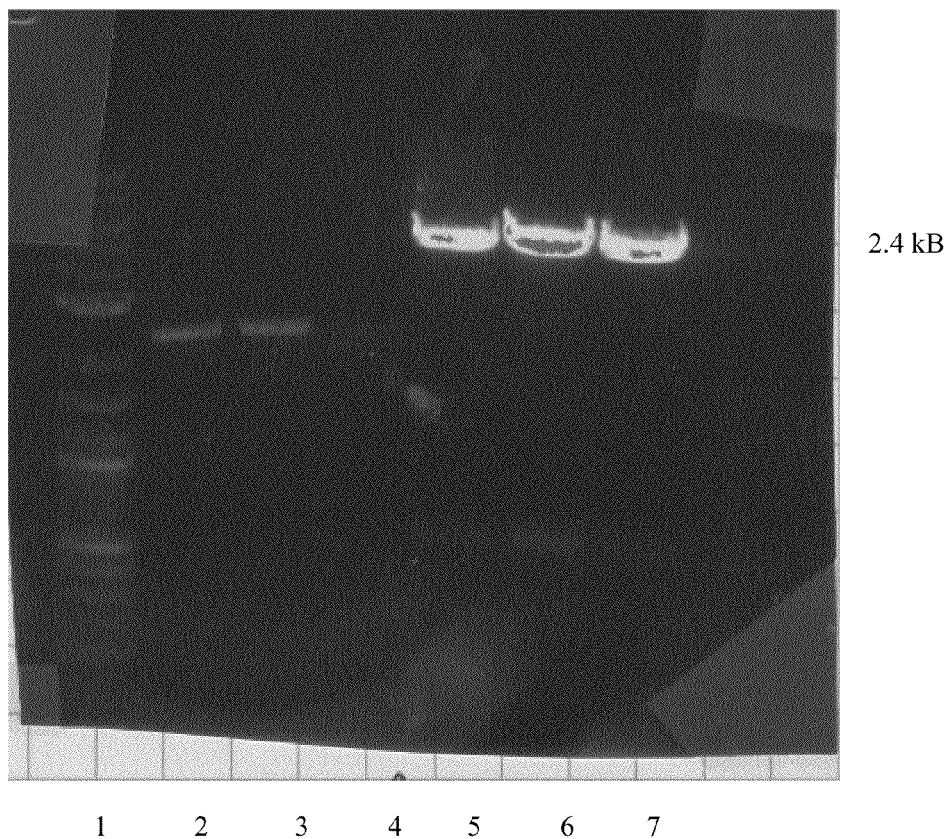
FIG. 3 illustrates the results of the OtsA/OtsB trehalose biosynthesis genes amplification by PCR from the E. coli genomic DNA. The OtsA/OtsB genes (lanes 2-4) appear at approximately 2.4 kb as indicated by the DNA ladder (lane 1). The digested pBAD18 vector used for cloning is in lanes 5-7.

PCR amplification of the OtsA/OtsB genes from genomic *E. coli* DNA 2-4) OtsBA amplified from genomic DNA using 5' and 3' primer sequences 5' GGGGAACCGAATTCATCACAGAACCGTTA 3' (SEQ ID NO: 5) and 5' GGGGAACCGAGCTCCTACGCAAGCTTTGG 3' (SEQ ID NO: 6) respectively. The PTC-100 Thermocycler (MJ Research; Waltham, Mass.) performed a segment at 95° C. for 5 minutes followed by 25 cycles at 95° C. for 1 minute, 55° C. for 45 seconds, and 72° C. for 2.5 minutes with a final extension at 72° C. for 10 minutes. The product was characterized using agarose gel electrophoresis. FIG. 3 shows the PCR product of the OtsA/OtsB gene at approximately 2.4 kb. The OtsA/OtsB genes from *E. coli* were successfully amplified by PCR for cloning into *E. coli*, which was carried out with the vector pBAD18.

The products of PCR amplification are characterized and purified using agarose gel electrophoresis. For example, 1% w/v agarose gel was run in a Bio-Rad Mini Sub-Cell Agarose Gel Electrophoresis Chamber (Hercules, Calif.) at approximately 120 volts in a 1X TBE buffer. Ethidium bromide (Patchogue, N.Y.) with a final concentration of 0.5 μg/ml was used to stain the gel. Each PCR sample obtained was loaded into the wells with 10× loading dye. These samples were run against 2.5 it of 2-log DNA Ladder (0.1-10 kb) (New England Biolabs; Ipswitch, Mass.). The agarose gels were imaged to detect the desired products using a Bio-Rad Chemidoc Imager (Hercules, Calif.).

Following agarose gel electrophoresis, the PCR products of the TreS, TreY/TreZ, and OtsA/OtsB genes were purified by gel extraction using a Zymoclean Gel DNA Recovery Kit (Zymo Research; Orange, Calif.). The protocol provided with the kit by Zymo Research was followed.

Figure 4:
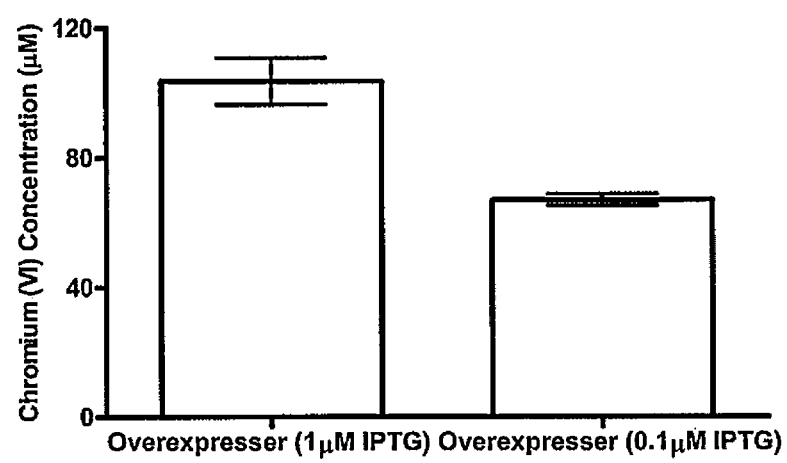
FIG. 4 illustrates the discovery that IPTG-induced overproduction of trehalose is harmful to *E. coli*. Decreasing the concentration of IPTG which induces the OtsA/OtsB genes in the overexpresser resulted in improved reduction of Chromium (VI).

Initially, the inventors intended to use the pET29b vector, which requires induction by isopropyl-β-D-thio-galactoside (IPTG) and results in very high production of the induced gene. The TreS gene from *M. smegmatis* was successfully amplified for future cloning into *E. coli* using a pET29b vector. However, the inventors found that IPTG-induction (which induces expression of the OtsA/OtsB genes in the overexpresser) was harmful to the *E. coli*, and decreasing the amount of IPTG improved Chromium (VI) reduction (FIG. 4). When using the higher concentration of 1 μM IPTG, less Chromium (VI) was reduced than when using 0.1 μM IPTG. Therefore, the inventors decided to use vectors induced by arabinose instead, and switched to the arabinose-induced pBAD-GFPuv vector.

The pBAD-OtsA/OtsB and pET-OtsA/OtsB plasmids were isolated and purified using a Zyppy Plasmid Miniprep Kit (Zymo Research; Orange, Calif.) in cultures of *E. coli* cells incubated in LB medium supplemented with ampicillin, cultured overnight with shaking at 37° C. Purification was conducted according to the Zyppy Plasmid Miniprep Kit protocol.

The pBAD-OtsA/OtsB plasmid construction was conducted with a 50 μl restriction digest using 5 μl of the pBAD-GFPuv plasmid, 2 units of NheI (New England Biolabs), 2.5 units of Buffer 2 (New England Biolabs), 2.5 μl 10×BSA, and 38 μl of sterile water. The digest was incubated at 37° C. overnight. A 50 μl restriction digest was conducted using 8 μl of the purified OtsA/OtsB genes, 2 units of NheI (New England Biolabs), 2.5 units of Buffer 2 (New England Biolabs), 2.5 µl of 10×BSA, and 35 µl of sterile water. The digest was incubated at 37° C. overnight. These digests were also attempted using 1 µl of BmtI as the enzyme (without BSA and bringing the final volume to 50 µl using sterile water). The OtsA/OtsB gene was ligated into the pBAD plasmid by incubating 2 µl of 10× T4 DNA Ligase Buffer, 5 µl of the pBAD restriction digest, 8 µl of the OtsA/OtsB restriction digest, 1 µl of T4 Ligase, and 34 µl of sterile water at room temperature for 4 hours.

Competent DH5α or XL1-Blue E. coli cells were transformed with the pBAD-OtsA/OtsB plasmid. The cells were incubated on ice for 10 minutes with the pBAD-OtsA/OtsB plasmid construct and heat shocked in a water bath at 42° C. for 30-45 seconds. This was followed by the addition of preheated LB medium. The cells were incubated at 37° C. for 45-60 minutes with shaking. To assay the cells for successful transformation, approximately 100 µl of the cells were plated on LB-Amp plates that were incubated at 37° C. overnight, because only transformed cells would be ampicillin-resistant and grown on LB-Amp plates.

The colonies of transformants were grown in LB media cultures overnight supplemented with ampicillin. The plasmid was isolated and purified using a Zymo Research Miniprep Kit. Restriction digests of the obtained plasmid using Bind were incubated overnight at 37° C. The digests were analyzed by agarose gel electrophoresis.

An OtsA knockout strain of *E. coli* was used for comparison in tests with wild type and OtsA/OtsB overexpressing *E. coli*. The knockout is unable to synthesize trehalose. Knockouts can be made with methods known in the art, such as by transposon insertion, or may be obtained from well-known repositories such as the Coli Genetic Stock Center (CGSC) at Yale University (New Haven, Conn.). The OtsA knockout was created by a Tn10 transposon insertion in the center of the OtsA gene, disrupting its sequence and obliterating its function. The Tn10 transposon carries a chloramphenicol resistance gene, conferring resistance to the antibiotic chloramphenicol.

In order to measure *E. coli* growth and viability when stressed and unstressed with Chromium (VI), cultures of the wild type, OtsA knockout, and OtsA/OtsB overexpresser from the MC4100 strain of *E. coli* containing 0 or 1000 µM hexavalent chromium were incubated at 37° C. with shaking in LB medium with 0.1 µM ampicillin and 1 mM arabinose. Growth was assayed every 24 hours by measuring the $A_{660}$ using a Beckman DU-640 UV-Vis Spectrophotometer (Beckman Coulter; Fullerton, Calif.). From these data, growth curves were obtained and compared using Graph Pad Prism 5 Software (Graph Pad Software; La Jolla, Calif.).

Figure 5:
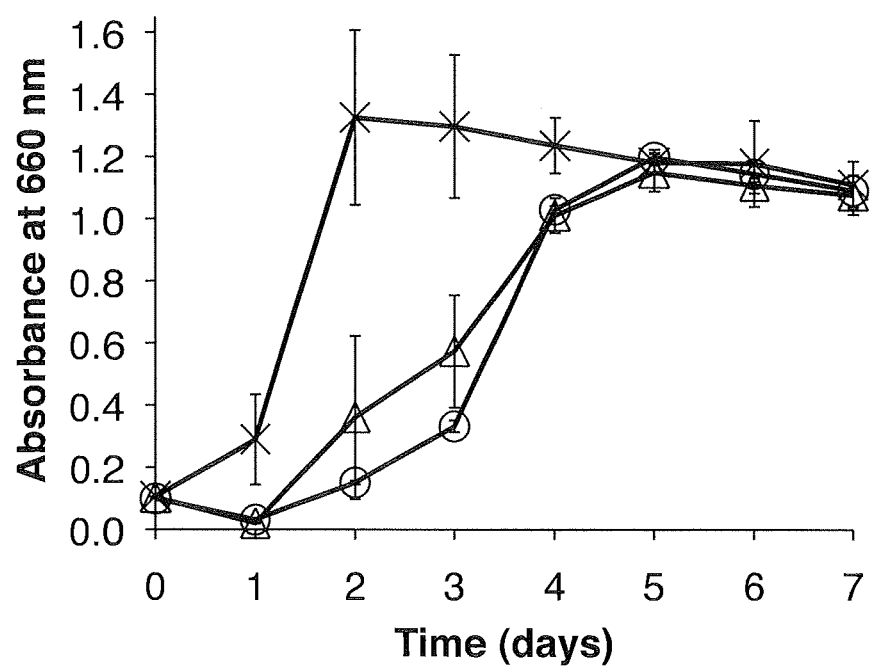
FIG. 5 shows that increased trehalose production improves viability in the presence of oxidative stress. Growth of the trehalose overexpresser (indicated by X), wild type (indicated by O), and trehalose knockout (indicated by triangle) are similar in the absence of stress, but the trehalose overexpresser showed improved viability when challenged with toxin (1000 μM hexavalent chromium) over an extended period.

Over a 7 day period, it was observed that in the presence of stress from 1000 µM hexavalent chromium, the trehalose overexpresser demonstrated higher viability than both the wild type and trehalose knockout (FIG. 5). Surprisingly, the stressed OtsA knockout showed similar growth to the wild type. This is presumably attributed to the lack of activation of the OtsA/OtsB trehalose biosynthesis pathway of the wild type *E. coli*. It has previously been shown that both osmotic and thermal stress activate trehalose biosynthesis but according to these results, surprisingly, it appears that oxidative stress exerted on *E. coli* does not have this same ability. Therefore, we presume that the wild type, like the trehalose knockout, was unable to generate trehalose. The expression of the OtsA/OtsB pathway in the overexpresser, however, was induced using arabinose. These results were obtained in triplicate.

In order to measure *E. coli* reduction of Chromium (VI) when stressed and unstressed with Chromium (VI), cultures of the wild type, OtsA knockout, and OtsA/OtsB overexpresser from the MC4100 *E. coli* strain containing 1000 µM hexavalent chromium were incubated at 37° C. with shaking in LB medium with 0.1 µM ampicillin and 1 mM arabinose. The same cultures used to measure *E. coli* growth were assayed for residual Chromium (VI) using diphenylcarbazide, which reacts with Chromium (VI) but not with Chromium (III) in a concentration-dependent manner. The supernatant from these cultures was obtained using microcentrifuge to pellet cellular debris. To assay for residual Chromium (VI), 150 µl of 10% v/v $H_2SO_4$ and 25 µl of a 0.5% w/v solution of diphenylcarbazide and acetone were added to 850 µl of the supernatant and the resulting solution was measured for absorbance at $A_{540}$ using a Beckman DU-640 UV-Vis Spectrophotometer (Beckman Coulter; Fullerton, Calif.), with higher absorbance readings corresponding to darker shades of pink and higher levels of Chromium (VI). These measurements were obtained at every 24 hours. Controls of 1000 µM hexavalent chromium containing no bacteria were also assayed in this manner. Using the absorbance readings and a diphenylcarbazide standard curve to obtain the concentrations of Chromium (VI) in each sample, the amounts of Chromium (VI) reduced by the wild type, the OtsA knockout, and the OtsA/OtsB overexpresser were compared.

To determine whether increasing trehalose biosynthesis improves reduction capabilities of *E. coli* stressed with Chromium (VI), the residual Chromium (VI) in cultures of the trehalose knockout, wild type, and trehalose overexpresser grown in the presence of 1000 µM hexavalent chromium were measured. Diphenylcarbazide was employed to test for remaining Chromium (VI). The shade of pink depends on the quantity of Chromium (VI), with a darker shade corresponding to higher levels of Chromium (VI). The differences in these solutions can be quantified by measuring the absorbance of the solution at $A_{540}$ and comparing it to a standard curve to determine Chromium (VI) concentration.

Figure 6:
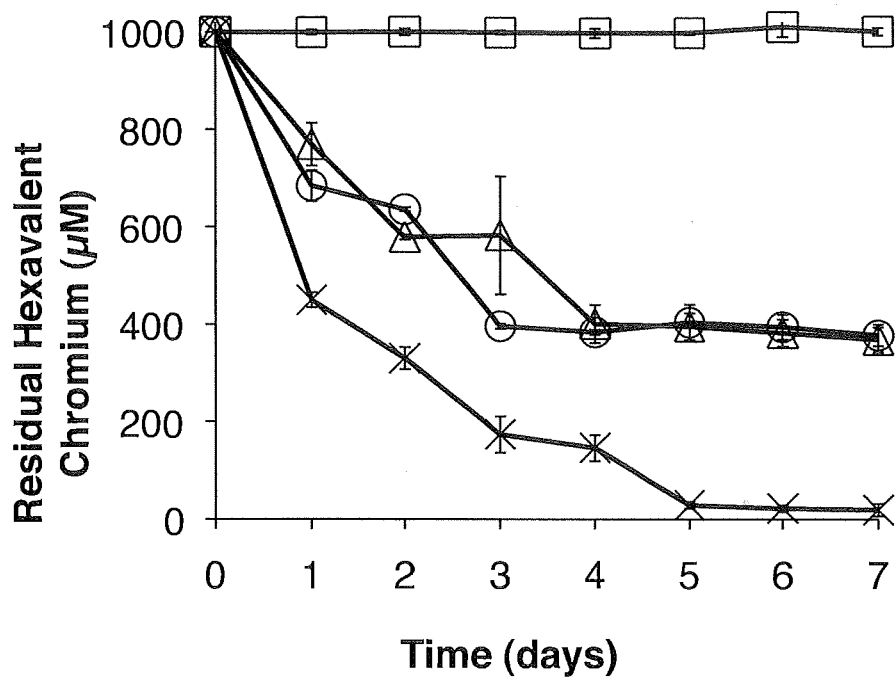
FIG. 6 demonstrates that increased trehalose production significantly increases the ability of *E. coli* to reduce Chromium (VI). The trehalose overexpresser (indicated by X) was effective in reducing Chromium (VI) while the wild type (indicated by O) and trehalose knockout (indicated by triangle) reduced Chromium (VI) less effectively. The squares indicate measurements taken of a bacteria-free abiotic control.

By growing *E. coli* with variable levels of trehalose production in the presence of oxidative stress, it was found that the trehalose overexpresser reduced significantly more Chromium (VI) than both the wild type and trehalose knockout controls (FIG. 6). This result demonstrates that higher levels of trehalose correspond to increased Chromium (VI) reduction.

However, FIG. 6 also shows that the wild type reduced about the same amount of Chromium (VI) as the OtsA knockout, probably due to lack of activation of the trehalose biosynthesis genes during oxidative stress. As such, trehalose production must be induced artificially in order to have any advantages for improved viability and efficacy during bioremediation. Trehalose expression of the OtsA/OtsB overproducer was induced using arabinose. Over a one-week period, the trehalose overexpresser reduced the Chromium (VI) almost entirely to Chromium (III) while the knockout and wild type reduced approximately half of the initial quantity of Chromium (VI). This shows that increasing trehalose content increases the rate of bioremediation of Chromium (VI). These results were obtained in triplicate.

The results of the present invention have been demonstrated above by genetically engineering *E. coli* to overexpress OtsA/OtsB. This allowed the inventors to study the effects of higher than normal trehalose levels on the survival and chromium reduction capabilities of *E. coli*. The inventors surprisingly discovered that trehalose accumulation is not stimulated by oxidative stress, but must be artificially induced in order to provide a protective effect on the bacteria. The inventors of the present invention also surprisingly discovered that inducing trehalose accumulation with high levels of IPTG had an adverse effect on bacteria under stress, necessitating inducing trehalose production by either lowered amounts of IPTG or alternative inducers such as arabinose. Increasing trehalose production in this manner improves bacterial defenses against oxidative stress, which in turn allows for improved reduction of toxins such as hexavalent chromium.

The present invention has been described with respect to various examples and embodiments herein, which are but representations of options for the present invention. That is, while the present invention is described in relation to the overexpression of trehalose in *E. coli*, it is not limited to that bacterium or to bioremediation of Chromium (IV). Instead, the present invention is directed to overexpressing trehalose biosynthesis genes in any bacteria capable of bioremediation to improve the viability of such bacteria stressed with toxins or pollutants. Moreover, the overexpression concept may be more generally applicable to other bioremediation applications. As such, it is to be understood that various modifications may be made without departing from the spirit and scope of the invention. All equivalents are deemed to fall within the scope of this description of the invention.

What is claimed is:

1. A genetically modified bacteria demonstrating improved survival under oxidative stress caused by toxins, wherein the genetically modified bacteria includes one or more inducible trehalose biosynthesis genes, resulting in increased trehalose production, wherein the inducible trehalose biosynthesis genes are exogenous to the genetically modified bacteria.

2. A genetically modified bacteria demonstrating improved survival under oxidative stress caused by toxins, wherein the genetically modified bacteria includes one or more inducible trehalose biosynthesis genes, resulting in increased trehalose production, wherein the inducible trehalose biosynthesis genes include inducible trehalose biosynthesis genes that are both endogenous and exogenous to the genetically modified bacteria.

3. The genetically modified bacteria of claim 1, wherein the genetically modified bacteria is *E. coli, B. subtillis, S. onesidensis*, or *G. metallireducens*.

4. The genetically modified bacteria of claim 1, wherein the genetically modified bacteria is *E. coli*.

5. The genetically modified bacteria of claim 1, wherein the genetically modified bacteria is *B. subtillis*.

6. The genetically modified bacteria of claim 1, wherein the inducible trehalose biosynthesis genes are induced by IPTG.

7. The genetically modified bacteria of claim 1, wherein the inducible trehalose biosynthesis genes are induced by arabinose.

8. A method of making a genetically modified bacteria demonstrating improved survival under oxidative stress caused by toxins, the method comprising: cloning one or more inducible trehalose biosynthesis genes into a bacteria, wherein the genetically modified bacteria demonstrate increased trehalose production and wherein the inducible trehalose biosynthesis genes are exogenous to the bacteria.

9. The method of claim 8, wherein the bacteria is *E. coli, B. subtillis, S. onesidensis*, or *G. metallireducens*.

10. A method of making a genetically modified bacteria demonstrating improved survival under oxidative stress caused by toxins, the method comprising: cloning one or more inducible trehalose biosynthesis genes into a bacteria, wherein the genetically modified bacteria demonstrate increased trehalose production, wherein the inducible trehalose biosynthesis genes include inducible trehalose biosynthesis genes that are both endogenous and exogenous to the genetically modified bacteria.

11. The method of claim 8, wherein the inducible trehalose biosynthesis genes are induced by IPTG or arabinose.

12. A method of reducing the concentration or form of a toxin in an environment, the method comprising:
treating the environment with genetically modified bacteria and an appropriate inducer, wherein the genetically modified bacteria includes one or more inducible trehalose biosynthesis genes, resulting in increased trehalose production.

13. The method of claim 12, where treating the environment with the genetically modified bacteria and an appropriate inducer includes introducing the genetically modified bacteria and inducer to the environment in situ.

14. The method of claim 12, where treating the environment with the genetically modified bacteria and an appropriate inducer includes introducing the genetically modified bacteria and inducer to the environment in a bioreactor.

15. The method of claim 14, wherein the toxin is Chromium (VI).

16. The method of claim 14, wherein the genetically modified bacteria is *E. coli* or *B. subtillis*.

17. The method of claim 14, wherein the inducible trehalose biosynthesis genes are endogenous to the genetically modified bacteria.

18. The method of claim 14, wherein the inducible trehalose biosynthesis genes are exogenous to the genetically modified bacteria.

19. The method of claim 14, wherein the inducible trehalose biosynthesis genes are both endogenous and exogenous to the genetically modified bacteria.

20. The method of claim 14, wherein the inducible trehalose biosynthesis genes are induced by IPTG or arabinose.

21. The genetically modified bacteria of claim 2, wherein the genetically modified bacteria is *E. coli, B. subtillis, S. onesidensis*, or *G. metallireducens*.

22. The genetically modified bacteria of claim 2, wherein the inducible trehalose biosynthesis genes are induced by IPTG.

23. The genetically modified bacteria of claim 2, wherein the inducible trehalose biosynthesis genes are induced by arabinose.

24. The method of claim 10, wherein the bacteria is *E. coli, B. subtillis, S. onesidensis*, or *G. metallireducens*.

25. The method of claim 10, wherein the inducible trehalose biosynthesis genes are induced by IPTG or arabinose.

* * * * *

```
SEQUENCE LISTING

<160> NUMBER OF SEQ ID NOS: 6

<210> SEQ ID NO 1
<211> LENGTH: 25
<212> TYPE: DNA
<213> ORGANISM: Artificial sequence
<220> FEATURE:
<223> OTHER INFORMATION: primer

<400> SEQUENCE: 1
attaggtacc tcattgctgc gctcc                                   25

<210> SEQ ID NO 2
<211> LENGTH: 25
<212> TYPE: DNA
<213> ORGANISM: Artificial sequence
<220> FEATURE:
<223> OTHER INFORMATION: primer

<400> SEQUENCE: 2
attagctagc atggaggagc acacg                                   25

<210> SEQ ID NO 3
<211> LENGTH: 25
<212> TYPE: DNA
<213> ORGANISM: Artificial sequence
<220> FEATURE:
<223> OTHER INFORMATION: primer

<400> SEQUENCE: 3
attacctgca ggcccggctg cggat                                   25

<210> SEQ ID NO 4
<211> LENGTH: 25
<212> TYPE: DNA
<213> ORGANISM: Artificial sequence
<220> FEATURE:
<223> OTHER INFORMATION: primer

<400> SEQUENCE: 4
attagctagc atgacgcgcc cggtg                                   25

<210> SEQ ID NO 5
<211> LENGTH: 29
<212> TYPE: DNA
<213> ORGANISM: Artificial sequence
<220> FEATURE:
<223> OTHER INFORMATION: primer

<400> SEQUENCE: 5
ggggaaccga attcatcaca gaaccgtta                               29
```

```
<210> SEQ ID NO 6
<211> LENGTH: 29
<212> TYPE: DNA
<213> ORGANISM: Artificial sequence
<220> FEATURE:
<223> OTHER INFORMATION: primer

<400> SEQUENCE: 6
ggggaaccga gctcctacgc aagctttgg                                29
```